US012806297B2

(12) United States Patent
Mounier et al.

(10) Patent No.: US 12,806,297 B2
(45) Date of Patent: Nov. 24, 2026

(54) TOOL FOR RETAINING FLUIDTIGHT TRANSFER BAGS IN AN AUTOCLAVE STERILISATION FACILITY

(71) Applicant: GETINGE LIFE SCIENCE FRANCE, Vendome (FR)

(72) Inventors: Cyril Mounier, Saint Armand Longpre (FR); Anne-Claude Gilbert, Vendome (FR); Nicolas Bosco, Guitalens-l'Albarède (FR)

(73) Assignee: GETINGE LIFE SCIENCE FRANCE, Vendome (FR)

(*) Notice: Subject to any disclaimer, the term of this patent is extended or adjusted under 35 U.S.C. 154(b) by 768 days.

(21) Appl. No.: 18/251,969

(22) PCT Filed: Oct. 29, 2021

(86) PCT No.: PCT/FR2021/051909
§ 371 (c)(1),
(2) Date: May 5, 2023

(87) PCT Pub. No.: WO2022/096811
PCT Pub. Date: May 12, 2022

(65) Prior Publication Data

US 2024/0016961 A1 Jan. 18, 2024

(30) Foreign Application Priority Data

Nov. 6, 2020 (FR) ........................................ 2011427

(51) Int. Cl.

| | |
|---|---|
| ***A61L 103/00*** | (2026.01) |
| ***A61L 2/07*** | (2006.01) |
| ***A61L 2/26*** | (2006.01) |

(52) U.S. Cl.
CPC .................................... *A61L 2/07* (2013.01); *A61L 2/26* (2013.01); *A61L 2103/23* (2026.01); *A61L 2202/122* (2013.01)

(58) Field of Classification Search
CPC .................................................. A61L 2103/23
See application file for complete search history.

(56) References Cited

U.S. PATENT DOCUMENTS 9,895,526 B2 * 2/2018 Korogi ................ A61M 39/165
2006/0088450 A1 4/2006 Stecklein et al.
(Continued)

FOREIGN PATENT DOCUMENTS

FR 2695343 A1 3/1994
JP 2915908 B1 7/1999
(Continued)

OTHER PUBLICATIONS

Japan Patent Office (JPO), Notice of Reasons for Rejection for Patent Application No. 2023-550721, drafted Jun. 16, 2025, Patent Examination Department, Japan.
(Continued)

*Primary Examiner* — Kevin Joyner
*Assistant Examiner* — Changru Chen
(74) *Attorney, Agent, or Firm* — McDonald Hopkins LLC

(57) ABSTRACT

Autoclave sterilisation facility for transfer bags is provided with a flexible container and with a rigid connection portion, the flexible container being connected to the rigid connection portion by a weld, the weld being contained in a plane, called the weld plane, substantially normal to the longitudinal axis of the connection portion, the facility including an autoclave sterilisation enclosure and a support including support plates configured to house in said enclosure, bags being intended to be disposed on the support plates, the rigid connection portion being oriented opposite the support plate
(Continued)

and a retention tool disposed on the bag in such a way as to limit the mechanical stress of the weld.

7 Claims, 6 Drawing Sheets

(56) References Cited

U.S. PATENT DOCUMENTS

| | | | | |
|---|---|---|---|---|
| 2010/0274256 | A1* | 10/2010 | Ritchey .................. | A61L 2/081 606/96 |
| 2016/0242453 | A1 | 8/2016 | Kato et al. | |

FOREIGN PATENT DOCUMENTS

| | | | |
|---|---|---|---|
| JP | 2000-023651 | A | 1/2000 |
| JP | 2000050848 | A | 2/2000 |
| JP | 2005013537 | A | 1/2005 |
| JP | 2015-089398 | A | 5/2015 |

OTHER PUBLICATIONS

China National Intellectual Property Administration (CNIPA), Notification of the First Office Action for Patent Application No. 202180082198.0, Jun. 30, 2025, Patent Examination Cooperation Center of the Patent Office, China.
International Search Report for Application No. PCT/FR2021/051909 dated Feb. 14, 2022.
Written Opinion for PCT/FR2021/051909 dated Feb. 14, 2022.

* cited by examiner

TOOL FOR RETAINING FLUIDTIGHT TRANSFER BAGS IN AN AUTOCLAVE STERILISATION FACILITY

This is the National Stage of PCT international application PCT/FR2021/051909, filed on Oct. 29, 2021 entitled "TOOL FOR HOLDING SEALED TRANSFER BAGS IN AN AUTOCLAVE STERILISATION FACILITY", which claims the priority of French Patent Application No. 2011427 filed Nov. 6, 2020, both of which are incorporated herein by reference in their entirety.

TECHNICAL FIELD AND PRIOR ART

The present invention relates to a tool for retaining bags in an autoclave sterilisation facility, more particularly bags for double-door fluidtight transfer systems.

In a certain number of industrial sectors, among which mention will be made of the nuclear, medical, pharmaceutical and agri-food sectors, it is necessary or desirable to carry out certain tasks in a confined atmosphere, either in order to protect the environment, for example from radioactivity, toxicity, etc., or on the contrary to be able to carry out these tasks in an aseptic or dust-free atmosphere, or finally both simultaneously.

Transferring devices or products from one closed volume to another, without at any time the fluid tightness of each one of these volumes with regards to the exterior being broken, poses a problem that is difficult to achieve. This problem can be resolved by a double-door connection device.

Such a double-door device provided with a multiple-safety control is for example known from document FR 2 695 343. Each volume is closed by a door mounted in a flange. Each door is engaged with its flange either by a bayonet connection, or by a hinge and a locking system and the two flanges are intended to be engaged with one another via a bayonet connection.

For example one of the closed volumes is formed by an isolator and the other volume is formed by a flexible container or fluidtight transfer bag.

Conventionally the connection portion carried by the isolator is designated as the alpha portion and the connection portion carried by the container is designated as the beta portion.

Seals are provided on the alpha portion and on the beta portion to ensure the fluid tightness between the connected volumes.

Such bags are usually intended for the sterile transfer of small components such as caps, syringe pistons, plastic bottles, etc., on the filling lines in the pharmaceutical industry.

The sterilisation can be a gaseous sterilisation by means of steam by an autoclave or by means of ethylene oxide (EtO).

The transfer bags adapted to sterilisation via autoclave or EtO comprise a flexible container including two faces, at least one of the faces forms a microbial barrier, impermeable to water but permeable to steam and to gas. For example, the flexible container includes a face formed by a non-woven textile sheet of high-density polyethylene fibres, for example marketed under the brand Tyvek® and a face made from extruded polyethylene.

The beta portion includes a flange, a door, a seal providing the fluid tightness between the flange and the door, and a clamping collar. A connector is welded on the edges of a cut-out formed in the face made of extruded polyethylene. The connector is assembled to the flange by means of the clamping collar.

The common temperatures applied during the autoclave cycles are approximately 120° C.-125° C. up to 134° C. in order to reduce sterilisation times. These temperatures are close to the fusion temperatures of the materials of the flexible container. Furthermore, pressure variation phases occur, which causes inflating and deflating phases of the flexible container.

Generally, sterilisation facilities include superimposed shelves that each receive at least one bag. In order to increase the number of bags sterilised per sterilisation cycle, the height of each shelf is reduced. However, during inflating phases, the bag located in a lower shelf presses against the bottom of the upper shelf. It cannot move freely which exerts mechanical tensions, in particular at the weld of the film of extruded polyethylene on the connector, such that they create a zone of weakness, which generates a risk of the film tearing during the sterilisation cycle or during manipulation of the bag, in particular during a connection of the bag to a fluidtight enclosure.

It is therefore sought to reduce the risk of this zone of weakness appearing.

DISCLOSURE OF THE INVENTION

It is consequently an aim of the present invention to offer means allowing for the autoclave sterilisation of bags for a double-door fluidtight transfer system limiting the risks of a zone of weakness appearing on the bag.

The aim mentioned hereinabove is achieved by means for retaining, in an autoclave sterilisation facility, bags for a double-door fluidtight transfer system including a connector and a flexible container, said means providing a retaining of the flexible container at its end provided with the connector in such a way as to reduce the effect of the traction forces on the weld between the connector and the flexible container.

The inventors have discovered that by retaining the bag at least during inflating cycles, the risk of a zone of weakness appearing was substantially reduced.

The retention tool makes it possible to preserve the integrity of the bag by protecting the weld line between the connector or the flange and the flexible container.

Particularly advantageously, the retaining means provide a reorientation of the traction forces that are exerted on the flexible container, the latter then being exerted substantially in the plane of the weld of the film on the connector, and not according to an angle in the sterilisation systems of the prior art. Thus the weld is less solicited during the inflating phases.

In a preferred embodiment, the retaining means include a tool provided with a face intended to come into contact with the face of the bag including the connector, the face comprising a first portion extending in a plane, this first portion being intended to be disposed on the side of the connector and a second portion extending the first portion and having a curvature intended to be oriented away from the bag.

The flat first portion provides an orientation of the traction forces in the plane of the weld between the connector and the flexible container and the second curved portion hugging the shape of the bag when it is inflating, provides a distribution of the forces over a large surface.

The rigidity of the first and second portions is sufficient to not be deformed under the action of the inflating of the bag.

Advantageously, the dimensions of the second curved portion are chosen with respect to the height of the shelf in such a way that the distance remaining free between the free end of the curved portion and the shelf located above limits and preferably prevents the folding of the bag over the tool.

The object of the present application is thus an autoclave sterilisation facility for bags provided with a flexible container and with a rigid connection portion with a longitudinal axis, said flexible container being connected to the rigid connection portion by a weld, said weld being contained in a plane, called the weld plane, substantially normal to the longitudinal axis of the connection portion, said facility including an autoclave sterilisation enclosure and a support comprising at least one support plate configured to house in said enclosure, at least one bag being intended to be disposed on the support plate, the rigid connection portion being oriented opposite the support plate and a retention tool intended to be disposed on the flexible container in such a way as to limit the displacement of the flexible container with respect to the rigid connection portion.

Preferably, the support includes several superimposed support plates and at least one retention tool associated with each support plate.

Advantageously the dimension of the retention tool in a direction orthogonal to a support plate is less than the distance between two superimposed support plates.

The object of the present application is also a retention tool for an autoclave sterilisation facility according to the invention, including a first portion provided with a flat face intended to be disposed in the vicinity of the rigid connection portion and in the vicinity of the bag in such a way that the flat face is in or is substantially in the weld plane, and a second portion provided with a curved face intended to be oriented by moving away from the support plate.

The tool preferably has a rigidity such that it is little deformed under the effect of the inflating of the bag during an autoclave cycle.

The transverse dimension of the first portion is advantageously at least equal to the transverse dimension of the flexible container of the bag.

According to an additional characteristic, the retention tool includes means for engaging with a support plate of the facility.

According to an additional characteristic, the retention tool includes means intended to at least partially surround the rigid connection portion of the bag.

For example, the first portion includes a polygonal section tube, the flat face being formed at least by a face of said tube and the second curved face includes a curved plate and reinforcements ensuring its rigidity.

The retention tool can include means for fastening to the rigid connection portion in a given relative position in such a way that the flat face of the first portion is contained in the weld plane.

The object of the present application is also an assembly of a support plate of a support for an autoclave sterilisation facility and of a retention tool according to the invention.

The support plate can include means cooperating with the means for engaging the retention tool.

The object of the present application is also an autoclave sterilisation method implementing the autoclave sterilisation facility according to the invention and the retention tool according to the invention, including:

Positioning at least one bag on a support plate.

Positioning the retention tool on said bag.

Positioning the support plate loaded with said bag and the retention tool in an autoclave enclosure.

Performing an autoclave cycle.

Removing said bag.

The autoclave sterilisation method advantageously applies to a fluidtight transfer bag.

BRIEF DESCRIPTION OF THE DRAWINGS

The present invention shall be better understood based on the following description and the accompanying drawings wherein.

DETAIL DISCLOSURE OF PARTICULAR EMBODIMENTS

In the following description, the invention shall be described in an application of retaining fluidtight transfer bags the flange of which is connected to the flexible container, for example by means of a clamping collar engaging the flange and a container welded on the flexible container. The invention also applies to the retaining of bags the flexible container of which is directly welded on the flange.

In the present application, the expression "substantially in the same plane" is used to qualify two elements located in the same plane or in two planes that have a low angle between them, the angle being less than 20°.

Figure 1A:
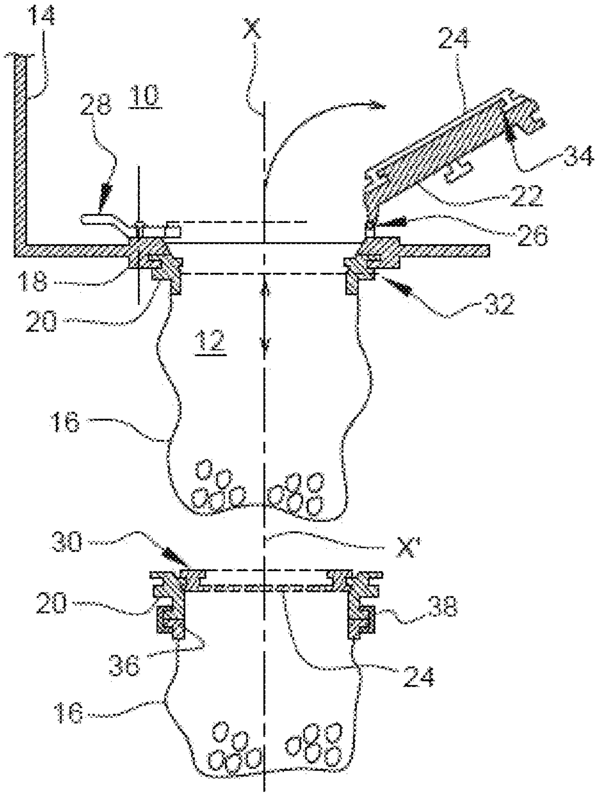
FIG. 1A is a longitudinal cross-section view that schematically shows the connection of a transfer bag on a cell by means of a double-door fluidtight transfer device.

FIG. 1A shows a schematic representation of a double-door fluidtight transfer system wherein a flexible transfer bag according to the invention can be implemented.

In general the double-door transfer system has a symmetry of revolution about the axis X which is the axis of the isolator flange.

In the following description, the two closed volumes that are to be connected correspond to an isolator 10 and to a flexible container 12 respectively.

The isolator 10 is delimited by a wall 14 of which only a portion is shown in FIG. 1A. It is equipped, conventionally, for example with remote means of handling such as remote manipulators and/or gloves (not shown) engaged with the wall 14, thanks to which the centralised control mechanism can be maneuvered from the inside of this cell 10. The container 12 is also delimited by a wall 16, as shown in particular in FIG. 1A. The wall 16 is formed by a flexible bag, for example obtained by welding via their edges two pieces of films, for example of rectangular shape. The bag includes an opening fastened in a sealed manner to a flange.

The double-door fluidtight transfer device mainly comprises an isolator flange 18, a container flange 20, an isolator door 22 normally closing off a circular opening delimited by the isolator flange 18, and a container door 24 normally closing off an opening delimited by the container flange 20. The isolator flange 18 and the container flange 20 are respectively fastened on the wall 14 of the cell 10 and on the wall 16 of the container 12. In this example, the door of the isolator 22 is articulated on the isolator flange 18 by a hinge 26.

Means generally designated by the reference 28, making it possible to control the opening and the closing of the doors 22 and 24.

For example, the fastening of the container door 24 on the container flange 20 is ensured by a bayonet connection 30 as is described in document FR 2 695 343. For example, in order to allow for the engaging of the container flange 20 on the isolator flange 18 and the engaging of the container door 24 on the isolator door 22, the double-door fluidtight transfer system also comprises two other bayonet connections designated respectively by the references 32 and 34. The three bayonet connections 30, 32 and 34 are arranged in such a way that after coming alongside of the container flange 20 on the isolator flange 18, a rotation of the container 12 about the axis thereof, for example in the clockwise direction, has the effect of engaging the container flange 20 and the isolator flange 18, engaging the container door 24 and the isolator door 22, and disengaging the container door 24 from the container flange 20. The latter two operations are carried out consecutively, in such a way that the opening of the container occurs only after the container door 24 has been engaged with the isolator door 22 to form a double door.

The assembly formed by the isolator flange and the isolator door is commonly designated as the "alpha portion".

Figure 1B:
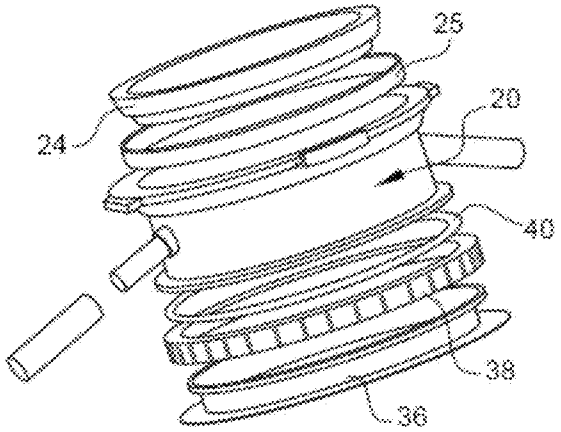
FIG. 1B is an exploded view of the beta portion alone.

The assembly formed by the container flange 20, the door of the container 24 and the seal 25, mounted on the flange and which ensures both the fluid tightness between the flange and the door and between the flange and the fluidtight transfer device, is commonly designated as the "beta portion". This assembly is shown in FIG. 1B. In this example, the beta portion also includes a connector 36 intended to be fastened to the flexible container, a clamping collar 38 to engage the connector and the flange and a seal 40 inserted between the flange 20 and the connector 36 in order to ensure the fluid tightness of the assembly.

The connector 36 includes an annular base 36.1 and a tubular sleeve 36.2. The annular base is intended to be welded to one of the sheets of the flexible container and the tubular sleeve is intended to engage the flange via the clamping collar.

During the creation of the weld, the annular base 36.1 and the sheet 46 are substantially in the same plane.

The transfer bag then includes a beta connection portion and a flexible container.

Figure 2A:
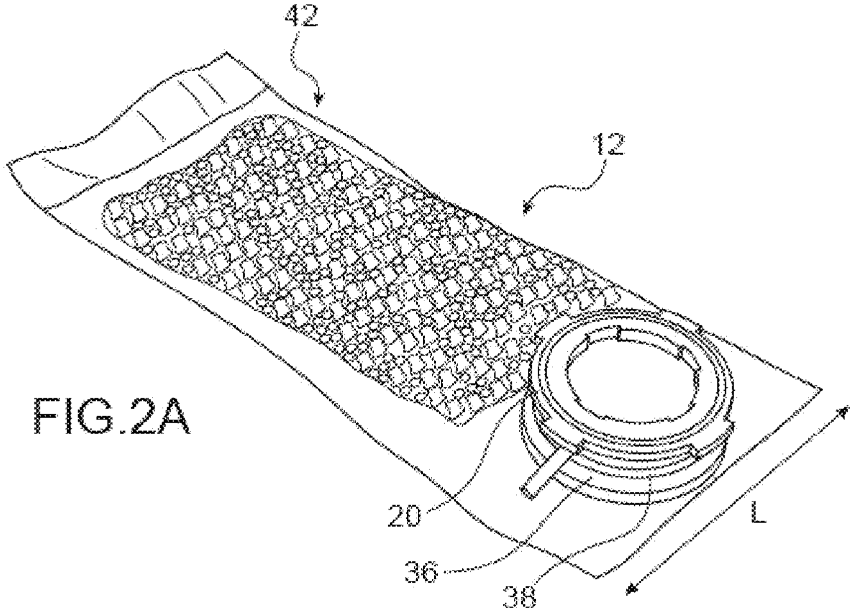
FIG. 2A is a perspective view of an example of a bag for a fluidtight transfer system that can be sterilised by an autoclave sterilisation facility.

FIG. 2A shows an example of a transfer bag 12 including a beta connection portion similar to the one of FIG. 1B and a flexible container 42.

Figure 2B:
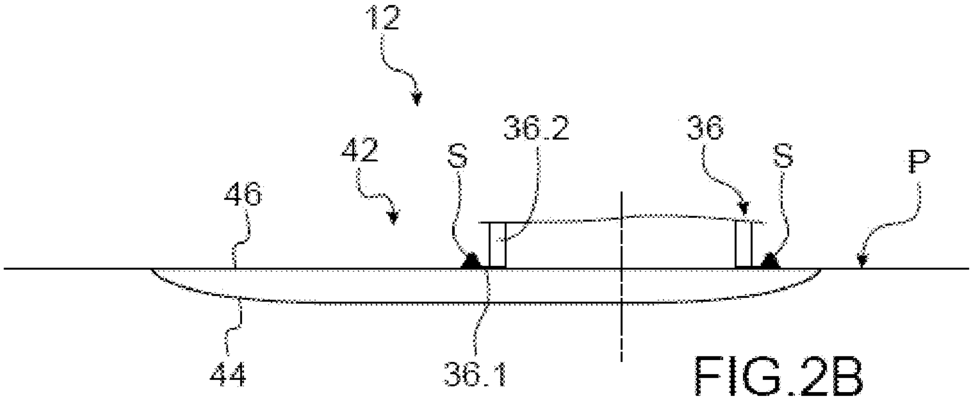
FIG. 2B is a side view of the connection zone between the connector and the flexible container.

FIG. 2B shows the flexible container 42 including for example a wall 44 made of non-woven textile of high-density polyethylene fibres, for example marketed under the brand Tyvek®, and a wall 46 made of extruded high-density polyethylene.

The two walls 44, 46 are sheets, rectangular in the example shown, superimposed and welded to one another at their outer edges. The shape of the sheets can be different, for example sheets in the shape of a disc are within the scope of the present invention.

The wall 46 includes an opening on the contour of which the connector 36 is welded.

FIG. 2B shows a detailed view of the weld S between the connector and the contour of the wall 46. The weld S is contained in a plane P.

The flange is assembled in a fluidtight manner on the tubular sleeve 36.2 of the connector 36 by means of the seal and of the clamping collar.

Figure 3A:
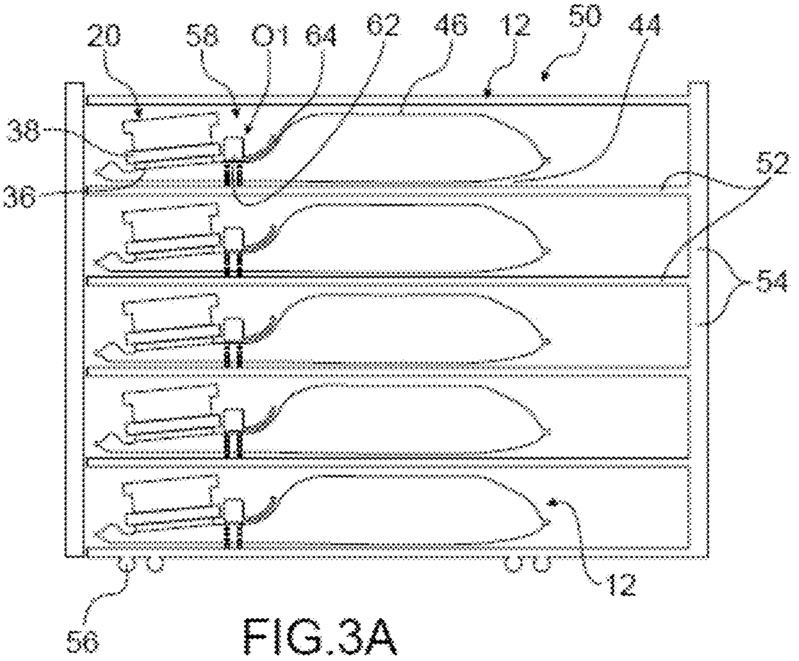
FIG. 3A is a side view schematically shown of an example of a support for an autoclave facility.

FIG. 3A shows a schematically represented side view of an example of a support for an autoclave facility loaded with transfer bags. In this representation, the bags are in the inflated state.

The support 50 includes several shelves, five in the example shown, each one loaded with a bag. Each shelf includes a support plate 52 on which the bag rests. The bag 12 is in contact with the support via its wall 44 that does not comprise the flange. The distance h between two support plates 52 is sufficient to house the flange of a bag without the latter coming into contact with the upper support plate. The support plates 52 are retained with respect to one another by vertical risers 54.

Preferably, the support plates 52 are perforated in order to allow for the circulation of a sterilising fluid.

Advantageously the support 50 is provided with castor wheels 56 in order to facilitate the positioning thereof and the removal thereof from the sterilisation enclosure.

The support 50 also includes, for each transfer bag, retaining means 58 configured to retain the bag, and more particularly the portion of the flexible container 42 located in the vicinity of the flange in such a way as to at least limit, advantageously prevent the displacement thereof so that the annular base 36.1, the weld S and the sheet 46 remain substantially in the same plane or in practically coinciding planes.

The retaining means 58 include a tool O1 comprising at least one first portion 60 intended to come into contact with the flexible container.

In this example, the first portion 60 includes a flat surface 62 formed at least by a face of a bar 63 of axis Y.

The width of the bar depends on the size of the bag. It is in general approximately a few centimetres, for example between 1.5 cm and 10 cm.

The tool O1 also includes a second portion comprising a curved face 64 extending the first flat face 62 and also intended to be in contact with the flexible container 42, mainly during the sterilisation phases during which the container inflates. The second curved face 64 hugs the bag when it is inflating. The radius of curvature is chosen to follow the natural radius of the bag when it is inflating and in such a way as to prevent the folding of the bag over the tool.

In this example, the tool O1 is fastened to the support plate on which the bag is placed. For example the tool O1 includes means 61 cooperating with means of the support plate in order to ensure the immobilisation thereof with respect to the plate. For example, the longitudinal ends of the bar 63 include holes for the passage of bolts that are screwed into the support plate, or the longitudinal ends include means that clamp the edges of the support plate. The tool O1 is then fastened to the support plate 52 on either side of the bag 12 by considering its axis X.

The forces that the tool O1 undergoes during an inflating phase of the bag are very substantial. For this the tool, more particularly the first flat face and the second curved face are carried out sufficiently rigid so to not be deformed or be little deformed when the bag inflates.

In this example, the first portion 60 includes a bar 63 formed by a tube with rectangular section, for example made of stainless steel, and having great rigidity to bending, and the second curved face 64 includes a curved steel sheet for example made of stainless steel. Reinforcements 65 are advantageously provided on the face of the sheet opposite the one intended to come into contact with the flexible container. In this example, the reinforcements 65 are vertical plates fastened to the tube and to the sheet for example by welding. The first flat face 62 and the second curved face 64 are welded to one another. Alternatively, a thick rigid sheet can be implemented both for forming the first flat face and/or the second curved face, such a tool would however have a higher mass. Again as an alternative, the first flat face and the second curved face are made from a single piece for example by a single sheet provided with reinforcements in order to give it sufficient rigidity.

The operation of the retention tool O1 shall now be described.

A bag 12 is disposed on a support plate 52 in such a way that the face of the bag not provided with the flange is in contact with the support plate 52.

The tool O1 is disposed above the bag on a zone located as close as possible to the flange 20 on the side where the flexible container extends. The first flat face 62 is intended to be bearing with the flexible container and is on the side of the flange.

The tool O1 is then fastened on the support plate 52 to fix the relative position of the tool and of the bag.

Transfer bags are disposed on all the support plates and a retention tool is positioned on each bag. In this example, the bags are loaded with elements which will then be sterilised simultaneously. In another example, the empty bags are sterilised.

The support plates are for example disposed above one another after the positioning of the bag and of the tool O1.

The support 50 is then disposed in a sterilisation enclosure (not shown).

The sterilisation cycle starts. The air in the enclosure is removed and is replaced with steam in order to saturate the volume of the enclosure. The pressure in the enclosure increases via injection of steam. The pressure in the enclosure varies during a sterilisation cycle causing inflations and deflations of the bags.

Figure 3B:
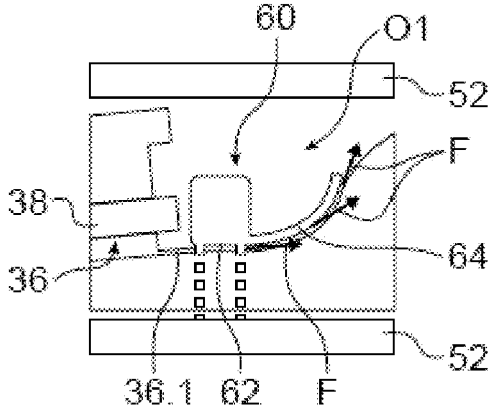
FIG. 3B is a detailed view of the facility of FIG. 3A at the retention tool.

When a bag inflates, thanks to the tool O1, it is retained in the zone close to the flange in such a way that the film 46 and the base 36.1 of the connector 36 remain substantially in the same plane. The film 46 then remains substantially in the plane of the weld S. Thus the traction forces F remain in the weld plane reducing the risks of damage to the latter (FIG. 3B).

Furthermore, when inflating, the film 46 hugs the first flat face 62 and the second curved face 64. The second curved face 64 provides a continuity with the first flat face 62 preventing the bag from coming into contact with a line that would weaken the bag. The traction force is distributed over the entire surface of the second curved face 64. The greater the radius of curvature of the second curved face 64 is, the more the traction forces exerted by the flexible container that is inflating are distributed over a large surface.

Thus thanks to this retention tool, the risk of a zone of weakness appearing around the flange is reduced.

The tool has a length l at least equal to the diameter of the connector 36, and preferably at least equal to the transverse dimension L of the bag 12, which makes it possible to prevent, when the bag inflates, rupture segments from appearing at the ends of the tool.

Preferably, when the bag 12 is disposed on a support plate 52 above which another support plate 52 is disposed and on which a bag can be in place, the free end of the second curved surface is located relatively close to the upper plate so as to prevent the bag from folding over the second curved portion.

Preferably, the free end of the second curved face 64 and the edge of the first flat face 62 oriented towards the connector are configured to limit the risks of damaging the bag. For example, the edge and the free end have, along a transverse section, a rounded section, of which the radius of curvature is sufficiently large to not risk deteriorating the bag.

Figure 6:
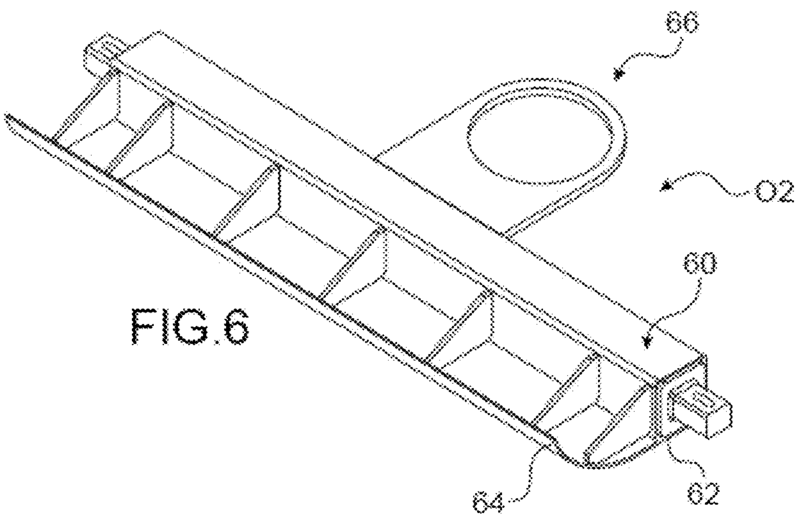
FIG. 6 is a perspective view of another example of a retention tool.

FIG. 6 shows another embodiment of the retention tool O2.

In this example, the retention tool is configured to cooperate with the beta portion. The retention tool O2 includes a part 66 in the form of a ring engaged with the first flat portion 60 and intended to surround the beta portion. The inner diameter of the ring 66 is slightly greater than the outer diameter of the beta flange, a clearance allows for the passage of the portion 66 around the flange. The ring makes it possible to fix the positioning of the tool with respect to the beta flange. Thus the beta flange no longer has any freedom of movement, which makes it possible to overcome the variability in the positioning of the bag on the shelf by the operator with respect to the retention tool.

Figure 7:
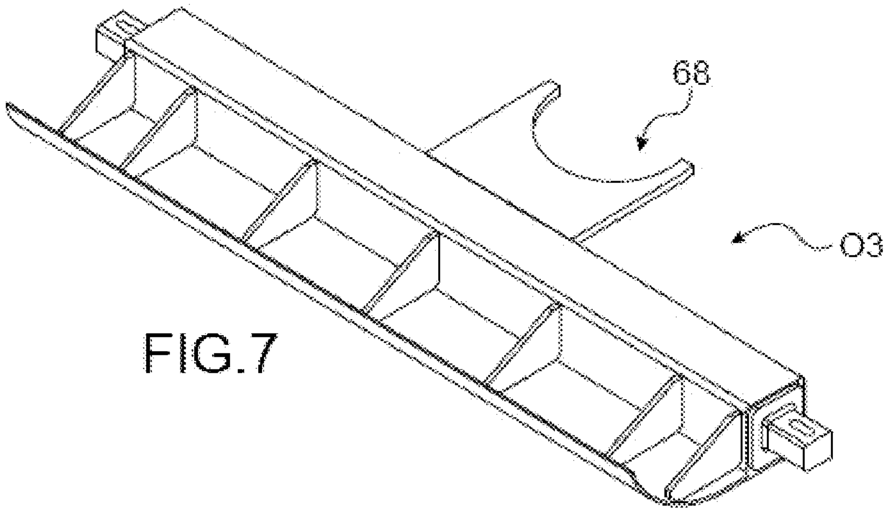
FIG. 7 is a perspective view of another example of a retention tool.

FIG. 7 shows another example of retention tool O3 including a part 68 engaged with the first flat portion and forming a housing partially surrounding the beta portion, for example over 180° or less. The part 68 makes it possible to position the flange in abutment on the tool and to suppress a variability in the positioning of the beta flange with respect to the tool. Furthermore, it offers facilitated positioning with respect to the ring.

Figure 8A:
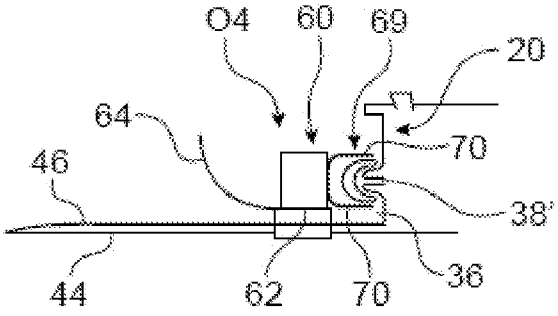
FIG. 8A is a side view of another example of a beta retention tool.
Figure 8B:
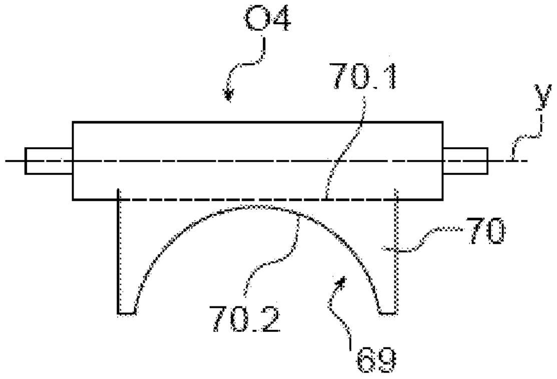
FIG. 8B is a top view of the retention tool of FIG. 8A.

FIGS. 8A and 8B show another example of retention tool O4 that is configured to be engaged with the beta portion of the transfer bag. The retention tool includes means for fastening 69 to the beta portion in such a way as to orient and to retain the first flat face 62 in the plane of the weld S.

In this example, the fastening means 69 include two parallel decks 70 between which the clamping collar of the beta portion is housed. Each deck 70 comprises a first straight edge 70.1 fastened onto a longitudinal face of the bar 63 and, opposite the first edge 70.1, a second edge 70.2 in the form of a concave arc of circle extending at most over 180° and with a radius such that the second edges 70.2 surround the beta portion on either side of the clamping collar. The two decks 70 are substantially parallel to the flat face.

When the clamping collar, mounted around the connector and the flange, is received between the two decks 70, the flange is positioned in abutment on the tool and suppresses a variability in the positioning of the beta flange with respect to the tool. An axial clearance can be provided between the clamping collar and the decks 70. Alternatively, it is retained between the decks for example by clamping or by snap-fitting.

The retention tool is then engaged with the bag, and the flat face parallel to the film 46 in the weld plane. When the bag inflates, since the orientation of the first flat face 62 is fixed with respect to the flange, it provides a retaining of the orientation of the traction force in the weld plane or substantially in the weld plane. The engaging of the retention tool with the beta portion has the advantage of allowing for a very good control of the relative position between the weld and the tool, more particularly of the first flat portion, since this position is fixed by the dimensions of the retention tool.

Alternatively, the fastening means 69 include a clamping collar intended to be mounted around the clamping collar 38 for example.

The tool O4 can be mounted on the flange before the positioning of the bag on the support plate 52 or after the positioning thereof on the support plate 52.

In the alternatives O2, O3 and O4, the retention tool is configured to be engaged with the support plate on which the bag is disposed. For example, it includes the fastening means similar to those of the tool of FIG. 4.

As the invention reduces the risks of damaging the weld via the traction of the bag, carrying out shorter autoclave cycles thanks to faster ramps for placing in a vacuum can be envisaged. Thus sterilisation productivity can be increased.

Moreover, the tool makes it possible to have a reduced inter-support plate space therefore it makes it possible to increase the number of bags per autoclave cycle.

Figure 4:
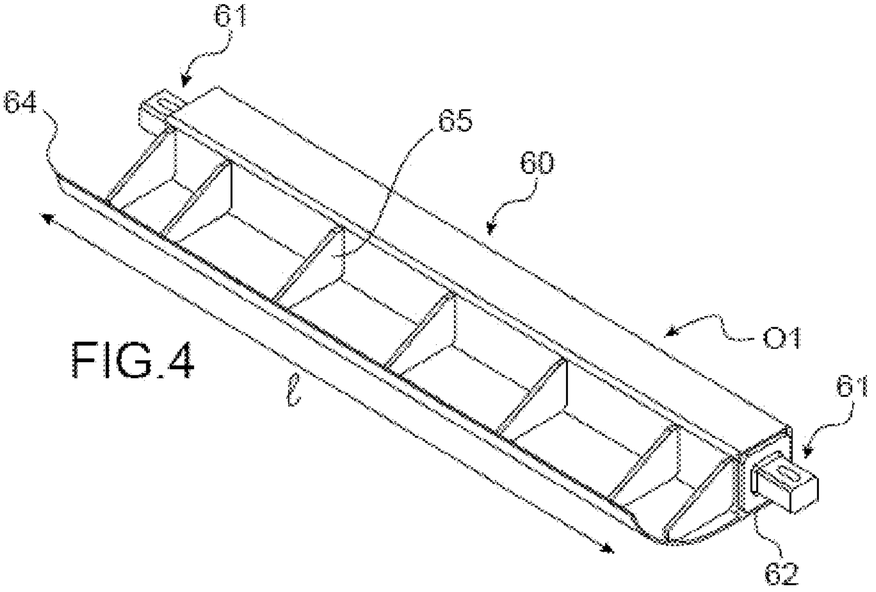
FIG. 4 is a perspective view of an example of a retention tool implemented in the autoclave facility.
Figure 5:
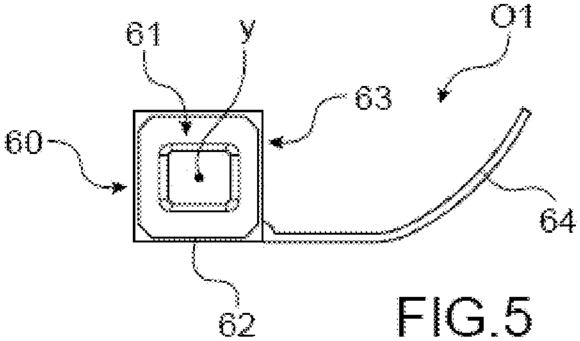
FIG. 5 is a side view of the retention tool of FIG. 4.

The tool of FIGS. 4 and 5 was described in an application for retaining a single bag. It can be applied to the retaining of several bags disposed next to one another, the bar 63 extending from one side to the other of the row of bags. Means for fastening the bar to the support plate between two bags can be envisaged.

In another embodiment, the retention tool is engaged with the support plate above. It is then positioned simultaneously to the stacking of the support plates and is directly positioned with respect to the bag below that it is intended to retain.

The tool is advantageously made from stainless steel offering substantial rigidity and very good resistance to sterilisation via autoclave (steam, temperature, pressure).

What is claimed is:

1. A retention tool for an autoclave sterilisation facility, the retention tool provided on a bag comprising a flexible container and a rigid connection portion with a longitudinal axis, said flexible container being connected to the rigid connection portion by a weld, said weld being contained in a plane, called a weld plane, substantially normal to the longitudinal axis of the connection portion, the bag disposed on a support plate, the rigid connection portion being oriented opposite the support plate, the retention tool disposed on the flexible container as close as possible to the connection portion and fastened to the support plate on either side of the bag in such a way as to limit a displacement of the flexible container with respect to the rigid connection portion, the retention tool including a first portion provided with a flat face disposed in a vicinity of the rigid connection portion and in a vicinity of the bag in such a way that the flat face is in or is substantially in the weld plane, and a second portion provided with a curved face oriented by moving away from the support plate.

2. The retention tool according to claim 1, wherein a transverse dimension of the first portion is at least equal to a transverse dimension of the flexible container of the bag.

3. The retention tool according to claim 1, including at least one hole configured to receive a bolt or at least one clamp configured to engage with the support plate.

4. The retention tool according to claim 1, including a ring configured to at least partially surround the rigid connection portion of the bag.

5. The retention tool according to claim 1, wherein the first portion includes a polygonal section tube, the flat face being formed at least by a face of said tube and wherein the second portion provided with the curved face includes an upper plate and reinforcements ensuring its rigidity.

6. The retention tool according to claim 1, including at least two parallel decks or a clamping collar configured to fasten the retention tool to the rigid connection portion in a given relative position in such a way that the flat face of the first portion is contained in the weld plane.

7. An assembly comprising the support plate of a support for the autoclave sterilisation facility and the retention tool according to claim 3, wherein the support plate includes at least one hole or at least one edge configured to engage with the the at least one hole or the at least one clamp, respectively, of the retention tool.

* * * * *